(12) United States Patent
Bhattacharya

(10) Patent No.: US 11,231,508 B2
(45) Date of Patent: Jan. 25, 2022

(54) GAMMA CAMERA DEAD TIME DETERMINATION IN REAL TIME USING LONG LIVED RADIOISOTOPES

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 365 days.

(21) Appl. No.: 15/315,107

(22) PCT Filed: Jun. 8, 2015

(86) PCT No.: PCT/IB2015/054323
§ 371 (c)(1),
(2) Date: Nov. 30, 2016

(87) PCT Pub. No.: WO2015/186117
PCT Pub. Date: Dec. 10, 2015

(65) Prior Publication Data
US 2017/0188982 A1  Jul. 6, 2017

Related U.S. Application Data

(60) Provisional application No. 62/008,791, filed on Jun. 6, 2014.

(51) Int. Cl.
*G01T 1/17* (2006.01)
*A61B 6/03* (2006.01)
*G01T 1/161* (2006.01)

(52) U.S. Cl.
CPC .............. *G01T 1/171* (2013.01); *A61B 6/037* (2013.01); *G01T 1/161* (2013.01)

(58) Field of Classification Search
CPC  G01T 1/171; G01T 1/161; G01T 1/20; A61B 6/037; A61B 6/06
See application file for complete search history.

(56) References Cited

U.S. PATENT DOCUMENTS 3,732,422 A   5/1973  Brunson et al.
4,058,728 A   11/1977 Nickles
(Continued)

FOREIGN PATENT DOCUMENTS

CN   101996344 A    3/2011
CN   103230282      8/2013
(Continued)

OTHER PUBLICATIONS

Ullmann et al. "Dead-time correction in dynamic radionuclide studies by computer," 1978, European Journal of Nuclear Medicine, vol. 3, pp. 197-202 (Year: 1978).*
(Continued)

*Primary Examiner* — Pascal M Bui Pho
*Assistant Examiner* — Patrick M Mehl

(57) ABSTRACT

For dead time determination for a gamma camera or other detector, a long-lived point source of emissions is positioned so that the gamma camera detects the emissions from the source while also being used to detect emissions from the patient. The long-lived point source, in the scan time, acts as a fixed frequency source of emissions, allowing for dead time correction measurements that include the crystal detector effects.

7 Claims, 2 Drawing Sheets

(56) References Cited

U.S. PATENT DOCUMENTS

| | | | |
|---|---|---|---|
| 5,132,540 A | | 7/1992 | Adolph et al. |
| 5,461,232 A | * | 10/1995 | McCandless .......... A61B 6/037 250/363.04 |
| 5,990,482 A | * | 11/1999 | Bertelsen .............. G01T 1/1648 250/252.1 |
| 5,999,588 A | * | 12/1999 | Shao ...................... G01T 1/171 250/363.04 |
| 6,008,493 A | * | 12/1999 | Shao ..................... G01T 1/1611 250/363.04 |
| 6,297,506 B1 | * | 10/2001 | Young .................. G01T 1/2985 250/369 |
| 6,410,920 B1 | * | 6/2002 | Shao ..................... G01T 1/1611 250/363.04 |
| 6,858,847 B1 | * | 2/2005 | Macciocchi .......... G01T 1/2985 250/363.03 |
| 2003/0128801 A1 | * | 7/2003 | Eisenberg et al. .............. 378/19 |
| 2007/0012879 A1 | * | 1/2007 | Testardi ................. G01T 1/161 250/361 R |
| 2007/0221850 A1 | * | 9/2007 | Panin .................... G01T 1/1617 250/363.04 |
| 2011/0220783 A1 | | 9/2011 | Tsukerman |
| 2013/0193330 A1 | * | 8/2013 | Wagadarikar ......... G01T 1/1648 250/362 |
| 2014/0003579 A1 | | 1/2014 | Berruyer |

FOREIGN PATENT DOCUMENTS

| | | |
|---|---|---|
| EP | 0 44 324 | 9/1991 |
| GB | 2 463 707 | 3/2010 |
| HU | 164766 B | 4/1974 |
| HU | 208749 B | 12/1993 |
| HU | 228836 B | 6/2013 |
| WO | 2008088326 | 7/2008 |

OTHER PUBLICATIONS

Inoue et al. "Estimation of deadtime in imaging human subjects," 1998, European Journal of Nuclear Medicine, vol. 25, pp. 1232-1237 (Year: 1998).*

Laere et al. "Non-invasive methods for absolute cerebral blood flow measurement using 99mTc-ECD: a study in healthy volunteers," 2001, European Journal of Nuclear Medicine, vol. 28, pp. 862-872 (Year: 2001).*

Woldeselassie "Precise real-time correction of Anger camera deadtime losses," Jul. 2002, Medical Physics, vol. 29, No. 7, pp. 1599-1610 (Year: 2002).*

Willowson et al. "Quantitative SPECT reconstruction using CT-derived corrections," 2008, Phys. Med. Biol., vol. 53, pp. 3099-3112 (Year: 2008).*

Beauregard et al. "Quantitative 177Lu SPECT (QSPECT) imaging using a commercially available SPECT/CT system," 2011. Cancer Imaging, vol. 11, pp. 56-66, 2011 (Year: 2011).*

Bailey et al. "Quantitative SPECT/CT: SPECT joins PET as a quantitative imaging modality," May 2014, Eur. J. Nucl. Med. Mol. Imaging, vol. 41, Suppl 1, S17-S25 (Year: 2014).*

Siman et al. "A revised monitor source method for practical deadtime count loss compensation in clinical planar and SPECT studies," 2015, Published Jan. 15, 2015, Physics in Medicine and Biology, vol. 60, pp. 1199-1216 (Year: 2015).*

Celler et al. 2014 Nucl. Med. Comm. 35:73-87 (Year: 2014).*

Siman et al. 2014 Int. J. Cancer Ther. Oncol. 2:020234 3 pages (Year: 2014).*

Fitzgerald et al. 2000 J. Nucl. Cardiol. 7:382-387 (Year: 2000).*

Carey et al. 2012 American Association of Physicists in Medicine report #181 46 pages (Year: 2012).*

Woldeselassie et al. 2002 Medical Physics 29:1599-1610 (Year: 2002).*

Beauregard et al. 2011 Cancer Imaging 11:56-66 (Year: 2011).*

Joshi 2007 PhD. Thesis University of Amsterdam, Netherlands, Chap. 4 p. 49-92 (Year: 2007).*

Pimlott et al. 2011 Chem. Soc. Reviews 40:149-162 (Year: 2010).*

Badawi et al. 2013 J. Inst. 8 P11005, 12 pages (Year: 2013).*

Unterweger 2002 Applied Radiation and Isotopes 56:125-130 (Year: 2002).*

Peterson et al. 2011 Phys. Med. Biol. 56 R145-R182 (Year: 2011).*

Guy et al. 2000 IEEE Nuclear Science Symposium. Conf. Record 2000:18/52-18/56 vol. 3 (Year: 2001).*

Hungarian Search Report for Hungarian Case No. P1600685/4 dated Mar. 21, 2017.

* cited by examiner

US 11,231,508 B2

GAMMA CAMERA DEAD TIME DETERMINATION IN REAL TIME USING LONG LIVED RADIOISOTOPES

RELATED APPLICATIONS

The present patent document claims the benefit of the filing date under 35 U.S.C. § 119(e) of Provisional U.S. Patent Application Ser. No. 62/008,791, filed Jun. 6, 2014, which is hereby incorporated by reference.

BACKGROUND

The present embodiments relate to single photon emission computed tomography (SPECT). In particular, the present embodiments relate to dead time correction in SPECT.

During SPECT imaging, the detector electronics take time to perform detection of an emission. During this period, additional emissions are not detected due to the unavailability of the detector electronics. As a result, the actual emissions may be under counted. The count of detected emissions is corrected for dead time. In one approach, a signal is input at fixed frequency and amplitude to the detector electronics. Due to the fixed frequency, a known number of signals is input. Due to dead time from detecting emissions from the patient, some of the fixed frequency signals are not detected. The ratio of detected ones of the fixed frequency to the input number provides a measure of dead time. The count of detected emissions from the patient is divided by the ratio to correct for the dead time.

Since the fixed frequency signal is input at the electronics, any contribution of the detector to the dead time is ignored. This contributes to uncertainty in the reconstructed image. In quantitative SPECT, an inexact correction may result in an inexact quantification. When imaging therapy isotopes with corresponding high-count rates, the inaccuracy may be more significant.

BRIEF SUMMARY

By way of introduction, the preferred embodiments described below include methods, systems, and non-transitory computer readable media for dead time determination for a gamma camera or other detector. A long-lived point source of emissions is positioned at a fixed location so that the gamma camera detects the emissions from the source while also being used to detect emissions from the patient. The long-lived point source, in the scan time, acts as a fixed frequency source of emissions, allowing for dead time correction measurements that include the crystal detector effects.

In a first aspect, a method is provided for dead time determination for a gamma camera. The gamma camera detects a count rate from a radioisotope source connected adjacent to the gamma camera and detects emissions from within a patient while detecting the count rate. The dead time is determined from the count rate. A count of the emissions is calculated as a function of the dead time.

In a second aspect, a SPECT system includes a shielded point source connected to emit radiation at a gamma camera. Detection electronics are configured to detect emissions, including the radiation from the shielded point source and radioisotope emissions from a patient. A processor is configured to correct for dead time of the detection electronics, the correction being a function of real-time detection of the radiation from the shielded point source.

In a third aspect, a method is provided for dead time determination for an emission detector. A detector detects first emissions from a patient and second emissions from a point source. The second emissions are subjected to dead time from the detection of the first emissions. A processor corrects a count of the first emissions as a function of a count of the second emissions.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A long-lived radioisotope is used for absolute system dead time determination in real time for a gamma camera. The detectors are exposed to the long-lived radioisotope at the time of patient acquisitions. Emissions from the long-lived radioisotope are regular and separable because of fixed spatial location and distinct emission energy from emissions in the patient by the radiotracer being imaged. The dead time is measured using the long-lived radioisotope, and the count of emissions from the radiotracer is corrected for the dead time. Real time measurement of the system dead time is incorporated as part of the input data from a patient scan, measuring the true system dead time at the time of the acquisition.

Figure 1:
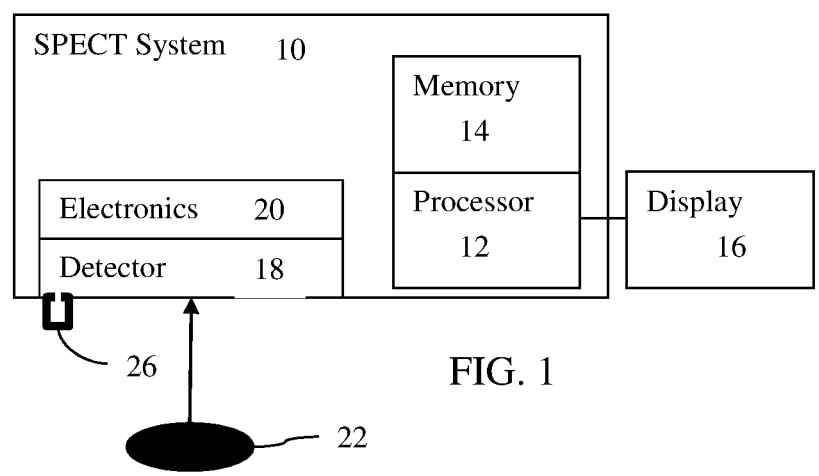
FIG. 1 is a block diagram of a SPECT system, according to one embodiment, with dead time correction.

FIG. 1 shows one embodiment of a single photon emission computed tomography (SPECT) system 10 for dead time correction. The system 10 includes a processor 12, a memory 14, a display 16, a detector 18, detector circuits or electronics 20, and a shielded point source 26. The processor 12, memory 14, and/or display 16 are part of the SPECT system 10 or are separate (e.g., a computer or workstation). Additional, different, or fewer components may be provided. For example, user input, patient bed, or other SPECT related devices are provided. Other parts of the system may include power supplies, communications systems, and user interface systems. Any now known or later developed SPECT system 10 may be used. As another example, the display 16 is not provided.

The detector 18 is a gamma camera connected with a gantry. The gamma camera may include the detector circuits or electronics 20 and the detector 18, or just the detector 18. The gamma camera is a planar photon detector, such as having crystals or scintillators with photomultiplier tubes or other optical detector. The gantry rotates the gamma camera about the patient. During scanning of a patient, emission events are detected with the camera at different positions or angles relative to the patient.

The detector 18 has any shape. For example, the detector 18 has a square or rectangular detection surface in a plane orthogonal to the patient. Other shapes may be used.

Figure 2:
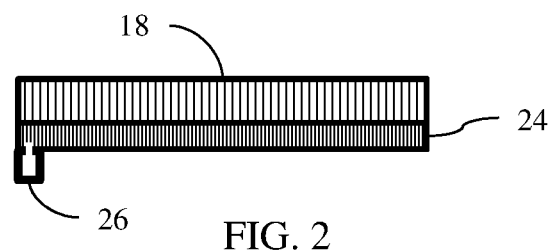
FIG. 2 is a cross-sectional side view of one embodiment of a detector and collimator with an added long-lived point source.

Referring to FIG. 2, a collimator 24 is positioned in front of, adjacent to, or by the detector 18. The collimator 24 is part of or connected to the detector 18. The collimator 24 includes lead, tungsten, or other material that is impervious to or absorbs and attenuates gamma radiation. The collimator 24 includes holes or other structures that pass gamma radiation from some directions (e.g., more orthogonal) and limit radiation from directions at other angles.

A shielded point source 26 is positioned relative to the detector 18. The shielded point source 26 is shielded in lead, tungsten, or other material preventing or limiting exposure to the patient. The shield may have a hole, window, or gap in shielding for allowing emissions of gamma rays from the shielded point source 26 to impinge upon the detector 18. Any size shielded point source 26 may be used, such as a 1 mm$^3$ vessel with the long-lived radioisotope. Line or other shaped sources may be used.

The point source 26 is a long-lived, factory-calibrated point source. The radioisotope of the point source 26 is long lived relative to the radioisotope ingested by or used for emitting gamma rays from the patient. If the half-life of the radioisotope is long enough (e.g., 6 months, 1 year, or more), then the rate of decay from the radioisotope is essentially constant during the patient acquisition for a given patient. The radioisotope of the point source 26 essentially acts as a fixed frequency signal but one that interacts with the entire imaging chain including the detector 18 and not just the signal processing detector circuit or electronics 20. Some example radioisotopes for the point source 26 include a single emission radioisotope, such as 182Hf with T1/2 of 8.9E6Y, E-Gamma of 270.4, and branching ratio (BR) of 79.0, or a multi-emission radioisotope, such as Ba133 with T1/2 of 10.55 y, E-Gamma of 81.0, 276.4, and 302.9+356.0+ 383.8 keV, and corresponding BR of 32.9, 7.2, and 89.3%, or 176Lu with T1/2 of 3.76E10y, E-Gamma of 88.3, 201.8, and 306.8, and corresponding BR of 14.5, 78.0, and 93.6. Other radioisotopes may be used.

The shielded point source 26 is connected to emit radiation at the detector 18 in a repeatable or known position. The connection is by weld, bolt, latch, press fit, threading, or other connection to the collimator 24, detector 18, gantry, frame, or other structure. The shielded point source 26 may be added to an existing detector 18 or collimator 24, such as adding a bracket to attach the point source 26 to a frame holding the detector 18. The shielded point source 26 may be designed to fit in or be part of the collimator 24. For example, a threaded hole is formed in the collimator 26. The shield of the shielded point source 26 includes matching threads for attaching.

The connection positions the shielded point source 26 so that the hole or window in the shielding is directed at the detector 18. The positioning angles the point source 26 to pass gamma emissions through the collimator 24 to the detector 18.

The point source 26 is positioned anywhere in front of the detector 18. In one embodiment, the point source 26 is positioned at a corner or other region that may not detect many gamma rays from the patient. Due to the collimation, the edge or corner of the detector 18 may be less likely to detect emissions from the patient. As a result, the shielded point source 26 is less likely to interfere with detection of emissions from the patient 22. Due to size, the point source 26 exposes or covers a small part (e.g., less than 1%) of the detector 18. The point source 26 is placed against or in the collimator 24 or is spaced from the collimator 24.

The detector electronics 20 include pulse arithmetic circuits, pulse height analyzer, digitizer, filter, analog-to-digital converter, application specific integrated circuit, field programmable gate array, signal processor, combinations thereof, processor 12, or other now known or later developed circuit for detecting the position and energy of each emission on the detector 18. A processor may be provided for pile-up handling. The detector electronics 20 receive the output of the photomultiplier tubes or other light detector of the detector 18 and output a position, time, and energy level. The detector electronics 20 may include a threshold function, filter, or other process for rejecting emissions due to unresolvable pile-up or energy not in an expected window or range for the radioisotope.

The detector electronics 20 detect emissions including the radiation from the shielded point source 26 and radioisotope emissions from a patient 22. Using a radioisotope marker (i.e., point source 26) for dead time determination during the patient acquisition does not require any modifications to detector electronics 20. The detector electronics 20 may apply a different energy range filter to distinguish between emissions from the point source 26 and the patient 22. For example, the radioisotope for the patient is Tc-99 m with peak energy of emissions at 140 keV, and the point source 26 uses 182 Hf with peak energy of emissions at 270.4 keV. By detecting the energy as being within 10% or other range of 140 keV, emissions from the patient are detected. By detecting the energy as being within 10% or other range of 270.4 keV, emissions from the point source 26 are detected. The detector electronics 20 or other processor counts the number of emissions for a given energy range. The count is an absolute count or is a count rate (i.e., number of emissions per unit time). The energies for the radioisotope of the point source 26 are separable or distinguishable from the energies of the radioisotope used in the patient 22. Emissions with energies outside the ranges are not counted or are discarded.

The detection by the detector 18 and detector electronics 20 occurs during a scanning session for a patient 22. The patient 22 is positioned within the gantry or on a bed of the SPECT system 10. For imaging uptake in a patient, the detector 18 detects emissions from the patient 22. The emissions occur from any location in a finite source (i.e., the patient 22). The radiotracer in the patient migrates to, connects with, or otherwise concentrates at specific types of tissue or locations associated with specific biochemical reactions. As a result, a greater number of emissions occur from locations of that type of tissue or reaction. For example, the radiotracer is designed to link with locations of glucose uptake, fatty acid synthesis, or other metabolic process. A given imaging session occurs during one scanning appointment and/or ingestion or injection of the radiotracer for a given instance of SPECT imaging.

In one embodiment, the detector electronics 20 performs pile-up separation. Emissions may occur rapidly enough in sequence that energy from one emission may result in a later emission appearing to have higher energy. By separating out the emissions and accounting for pile-up, emissions at the desired energies may be more accurately determined without discarding actual emissions that should be maintained. Since emissions from different energies are used (e.g., from the patient 22 and the point source 26), pile-up processing may alter the calculation of dead time. In one embodiment, the alteration is acceptable. In another embodiment, the pile-up processing is not used. Instead, the detector electronics 20 are operated without pile-up separation. A fully integrated mode (i.e., detect based on energy without attempting to account of energy tails from other emissions) is used.

The processor 12 is a general processor, digital signal processor, graphics processing unit, application specific integrated circuit, field programmable gate array, digital circuit, analog circuit, combinations thereof, or other now known or later developed device for processing emission information. The processor 12 is a single device, a plurality of devices, or a network. For more than one device, parallel or sequential division of processing may be used. Different devices making up the processor 12 may perform different functions, such as one processor (e.g., application specific integrated circuit or field programmable gate array) for reconstructing and another for correcting an emission count for dead time. In one embodiment, the processor 12 is a control processor or other processor of the SPECT system 10. In other embodiments, the processor 12 is part of a separate workstation or computer.

Figure 3:
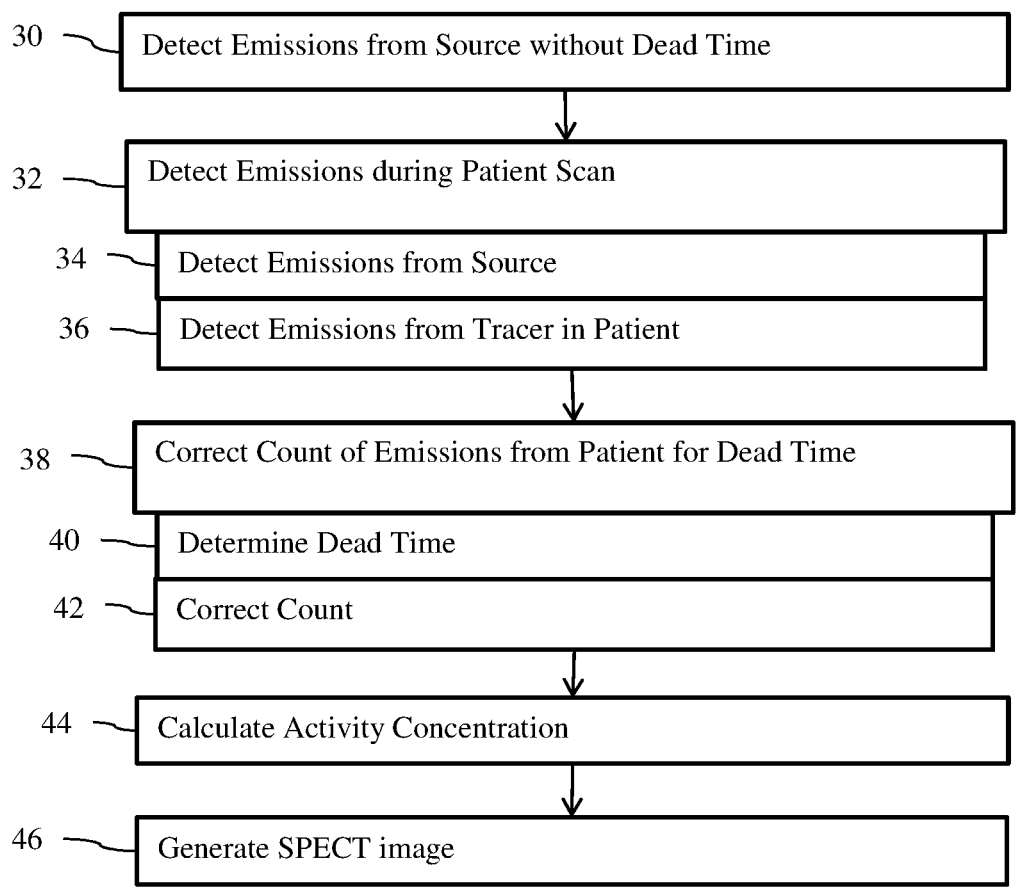
FIG. 3 is a flow chart diagram of one embodiment of a method for dead time determination for an emission detector.

The processor 12 operates pursuant to stored instructions to perform various acts described herein, such as performing acts 38, 44 and 46 of FIG. 3. The processor 12 is configured by software, firmware, and/or hardware to perform, control performance, and/or receive data resulting from any or all of the acts of FIG. 1.

In one embodiment, the processor 12 is configured to correct for dead time of the detector electronics 20. During the detection processing, the detector electronics 20, of which the processor 12 may be part, cause a delay. Any emissions occurring during the delay are not processed or are not detected. This delay of nanoseconds or microseconds is the dead time. To correct for the dead time, the processor 12 determines a scaling factor representative of the percentage or number of emissions that occur but are not detected due to dead time. The count of the detected emissions is increased based on the scaling factor.

In one embodiment, the processor 12 uses the real-time detection of the radiation from the shielded point source 26 for the correction. The count of the emissions from the shielded point source 26 is used. Since these emissions are detected while also performing operations to detect the emissions from the patient with the same detector, the emissions from the point source 26 are subject to the dead time of the detector electronics 20. The point source 26 generates emissions at a regular or known rate, so the number of emissions during the count of emissions from the patient is known.

Alternatively, the number of emissions from the point source 26 is measured at another time when there is no dead time, such as after calibrating the SPECT system 10 but without a phantom or patient (e.g., after each of monthly calibrations). The emissions from the point source 26 are measured when there are no emissions from a radiotracer in a patient. By measuring the count instead of using an assumed count, effects due to misalignment or other variables are more likely included in the count. The assumed or measured count from the detector 18 with no dead time is stored in the memory 14 for use in dead time correction.

The processor 12 calculates a ratio of a number of point source 26 emissions in a given time period during the scan of a patient to the number of emissions when there is no dead time. This ratio indicates the scale factor. The ratio indicates what percentage of actual emissions is missed due to dead time so that the detected count may be increased to account for dead time. The ratio of the count rate from the point source 26 during a patient acquisition to the count rate when there is no dead time provides the scale factor. Since the ratio depends on a measurement during patient scanning, the ratio is a real time measure of the system dead time at the time of patient acquisition. In other embodiments, a different function than a ratio is used.

The processor 12 is configured to scale the count of the emissions from the patient 22. Any or all counts are scaled, such as counts for each location on the detector. The count is scaled by the scaling factor. The ratio of counts from the point source 26 with and without dead time is used to scale the counts from the patient. The ratio of counts of emissions from the patient with and without dead time is the same as the ratio from the point source 26. The count from the patient without dead time is unknown, so the count of emissions from the patient with dead time is divided by the ratio of the emissions from the point source. For other functions than ratio, multiplication or other functions for adjusting or increasing the count of the emissions from the patient are used. By weighting the count of the radiotracer emissions from the patient based on the number of emissions of radiation from the point source 26, a more accurate count is provided.

For a given imaging session, a single correction is used. Alternatively, the ratio or scale factor is calculated for different periods, such as different positions of the detector 18 relative to the patient. The counts for each of the periods are corrected based on weights measured for that respective period.

The SPECT system 10, using the processor 12 or another processor, is configured to reconstruct the imaged volume by applying a system matrix or forward projection to the corrected counts. The emissions from the patient, as corrected for dead time, are used in reconstruction. Any reconstruction may be used to estimate the activity concentration in the patient. The SPECT system 10 accesses the detected emission events from the memory 14 or buffers to reconstruct. Based on the corrected counts for the emission bins from different locations on the detector, the processor 12 is configured to calculate specific uptake values (SUVs) as a function of location in the patient. The SUV at one or more locations are calculated by normalizing the activity concentrations as represented by the counts with a dose for the radioisotope in the patient 22. Alternatively, activity concentration without SUV is used in the reconstruction.

The detected emission events, other functional information, or other scan data is stored in the memory 14. The data is stored in any format. The memory 14 is a buffer, cache, random access memory (RAM), removable media, hard drive, magnetic, optical, database, or other now known or later developed memory. The memory 14 is a single device or group of two or more devices. The memory 14 is part of SPECT system 10 or a remote workstation or database, such as a picture archiving and communications system (PACS) memory.

The memory 14 may store data at different stages of processing, such as a count and counting period from the point source 26 without dead time, count and period during patient scanning, raw data (e.g., energy and location) representing detected emissions from the patient without further processing, filtered or thresholded data prior to reconstruction, reconstructed data, filtered reconstruction data, a system matrix, forward projection information, projection data, thresholds, an image to be displayed, an already displayed image, or other data. The memory 14 or a different memory stores the ratio or other scale factor for correcting for dead time. The memory 14 or a different memory stores the corrected counts of emissions from the patient. For processing, the data bypasses the memory 14, is temporarily stored in the memory 14, or is loaded from the memory 14.

The memory 14 is additionally or alternatively a non-transitory computer readable storage medium with processing instructions. The memory 14 stores data representing instructions executable by the programmed processor 12. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, central processing unit (CPU), graphics processing unit (GPU), or system.

The display 16 is a cathode ray tube (CRT), liquid crystal display (LCD), plasma screen, projector, printer, or other output device for showing an image or quantity. The display 16 displays an image of the reconstructed patient volume, such as showing activity concentration as a function of location. The uptake function (e.g., SUV) of the tissues of the patient may be represented in the image. Multi-planar reconstruction, 3D rendering, or cross-section imaging may be used to generate the image from the voxels of the reconstructed volume. Alternatively or additionally, any quantities derived by the processor 12 may be displayed, such as SUVs and/or change in SUV. Other quantities may be determined, such as average SUV or activity concentration for a region, maximum SUV, peak SUV in a predetermined unit volume, variance in activity concentration, or total SUV. The image values or quantity is based on counts that have been corrected for dead time in real-time using the point source 26.

FIG. 3 shows one embodiment of a method for dead time determination for a gamma camera or other emission detector. The dead time is determined and used to correct emission counts in qualitative and/or quantitative SPECT. Real-time measure of dead time is used to correct the number of detected emissions from the patient. The method is applied for a given scan of a given patient.

The method is implemented by the system of FIG. 1, the arrangement of FIG. 2, both, or other system and arrangement. A processor performs acts 38-46. A gamma camera or detector and detector electronics perform acts 30-36. A long-lived source is used for performing acts 30, 32, and 34. A radiotracer is used to perform acts 32 and 36. Other devices or materials may be used or controlled to perform any of the various acts.

Additional, different, or fewer acts may be performed. For example, act 30 is not performed where the number of emissions from the long-lived source is assumed or simulated. As another example, acts 44 and/or 46 are not provided. In other examples, acts related to positioning the patient, configuring the SPECT scanner, and/or SPECT imaging are provided. The acts are performed in the order shown or a different order.

In act 30, emissions from a long-lived source are detected. A gamma camera or other detector detects emissions from a shielded source positioned by the detector. As part of calibration or other time in which emissions from other radioisotopes are not also being detected, emissions from the long-lived source are detected. A count over time or rate of emission is determined. The determination is made while the detector and electronics are not subjected to dead time. The emissions are measured to establish a base line count rate for the long-lived source. In alternative embodiments, the count rate from the long-lived source is assumed or simulated. The count rate is stored and later loaded from memory.

In act 32, emissions are detected during a scan of a patient. During the scan, the gamma camera or other detector detects emissions from any source. The emissions are from the long-lived source and from a radioisotope in the patient. The emissions from the long-lived source are detected at a corner or other position relative to the detector. By placing a shielded source to direct emissions to the detector, the emissions may be detected. The radioisotope in the patient is an injected or ingested liquid tracer. Emissions from the different radioisotopes are detected during the scan of the patient.

The emissions from both sources during the patient scan are subjected to dead time. The long-lived source may generate emissions periodically, but with enough separation to avoid dead time in the detection. The emissions from the radioisotope in the patient may be less regular and may occur with variable amounts of separation in time. Due to the emissions from the patient, other emissions from the patient and/or emissions from the long-lived source may not be detected due to dead time. Some emissions from both sources are missed by the detector and detection electronics.

During the time in which a patient is scanned (i.e., while the patient is positioned for scanning), the emissions are detected in real-time. As the emissions from the patient and the long-lived source occur, at least some of the emissions are detected.

Energy distinguishes the emissions from the different sources. The detection electronics threshold or window energies within different ranges. One range is provided for detecting emissions from the radioisotope in the patient. Another range is provided for detecting emissions from the long-lived source. The energy ranges do not overlap, allowing distinguishing between the sources of the emissions. A count and/or count rate of the emissions is separately measured by the detector and detection electronics for each source.

The gamma camera, such as the detection electronics of the gamma camera, operates in a fully integrated mode. For SPECT, the fully integrated mode avoids pile-up processing. Rather than separate out emissions with pile-up processing, emissions are either in or not in the energy window. If multiple emissions pile up, then one or more of the emissions may be detected as having an energy outside the range or ranges of interest. As a result, the emission is not counted without pile-up processing. By operating in the fully integrated mode, distinguishing between emissions from sources at different energies is avoided. Alternatively, pile-up processing is provided.

Act 32 is represented in FIG. 3 as including acts 34 and 36. Additional, different, or fewer acts may be provided for detecting emissions during the patient scan. Acts 34 and 36 are performed in any order in an on-going or repeating manner.

In act 34, emissions from a long-lived source are detected. The source is positioned adjacent to the gamma camera. The gamma camera detects the emissions. By having a greater half-life by a factor of at least ten (e.g., half-life in months or years) than a radioisotope in the patient (e.g., half-life in hours or days), the resulting emissions may be treated as a fixed frequency signal over the patient scan.

The processor or detection electronics determine a count and/or count rate for the emissions from the long-lived source. The number of emissions or number over a period is calculated.

In act 36, emissions from within the patient are detected. As the radioisotope in the patient decays, gamma radiation is emitted. The gamma camera detects the emissions.

The detection occurs while detecting the emissions from the long-lived source. The emissions may occur at a same time or different times. Each detected emission results in dead time. Any following or subsequent emissions occurring in the dead time are not detected. The detection of the emissions continues during the patient scan with some emissions being missed.

In act 38, one or more counts of emissions from the patient are corrected. A processor increases the count to account for emissions that occurred during the dead times. Since emissions during the dead times are not detected, the correction instead relies on a count or count rate of emissions from the long-lived source while subjected to the same dead times. The count or count rate while not subjected to the any dead time may also be used. The counts for each of different positions on the detector are corrected.

Act 38 as represented in FIG. 3 includes acts 40 and 42. Additional, different, or fewer acts may be performed to correct based on the detections of acts 30-36.

In act 40, a dead time is determined from the count or count rate from the long-lived source based on the detections of act 34. The dead time is a ratio or percentage of time during which detections cannot occur as compared to the total. In one embodiment, the ratio of the count or count rate of act 34 (e.g., count from long-lived source subject to dead time) to the count or count rate of act 30 (e.g., count from long-lived source not subjected to dead time) is calculated. This ratio indicates the relative amount of dead time to overall time of scanning or counting emissions from the patient. The ratio relies, in part, on measures or detection in real-time with detection of emissions from the patient.

In act 42, the count of the emissions detected in act 36 is corrected. The emissions detected in act 36 are subject to undercounting due to the dead time. To more accurately reflect the number of actual emissions, the count is increased. The ratio from the long-lived source is indicative of the amount of undercounting. By dividing the count by the ratio, the processor corrects the count. The count is increased to account for emissions likely or possibly missed during the dead time. Other functions to increase the count by a scaling factor based on the detection of act 34 may be used.

In act 44, the processor calculates the activity concentration. The corrected count is used to estimate the activity at a given location or region in the patient. The activity concentration may be the corrected count or a number of the emissions for a given location. The activity concentration in a patient having received the liquid radiotracer is determined as part of reconstruction by the SPECT system. After ingesting or injecting the radiotracer into the patient, the patient is positioned relative to the detector and/or the detector is positioned relative to the patient. Emissions from the radiotracer within the patient are detected over time. To determine the locations within the patient at which the emissions occurred, the detected emissions, as corrected for dead time, are reconstructed into an object space.

For reconstruction, the activity concentration (e.g., quantitative SPECT) is reconstructed using a system matrix or forward projection. Distribution of emissions in a volume or image data is reconstructed from the detected emissions. The quantity or amount of uptake for each location (e.g., voxel) may be estimated as part of the reconstruction in computed tomography. The SPECT system estimates the activity concentration of an injected radiopharmaceutical or tracer for the different locations. In quantitative SPECT, the goal is to estimate the activity concentration in kBq/ml of the tracer (i.e., isotope) that was injected into and distributed within the patient.

The reconstruction is iterative and contains a model of the imaging formation physics as a pre-requisite of quantitative reconstruction. The image formation model includes the detected data (e.g., corrected counts), the system matrix or forward projection, isotope properties (e.g., dose value), and/or biology. The system matrix or forward projection represents mechanical properties of system, but may include other information (e.g., injection time and patient weight as represented by SUV).

Reconstruction includes a projection operator that is able to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, non-negative least squares (NNLS), or another approach.

Specific uptake values (SUVs) may be calculated. The activity concentration represents the amount of uptake at each location. This amount of uptake is a measure of emitted radiation, so is not normalized for the radiation dose provided to the patient. As a result, comparing uptake from different times may not be useful unless the same dose is provided. By calculating the SUV, uptake normalized for dose is provided, allowing comparison of different measures.

In act 46, a SPECT image is generated. The corrected count is used in the reconstruction. Where quantitative SPECT is not provided, the corrected count may be used without SUV and/or activity concentration calculation. For either quantitative or qualitative SPECT, the corrected counts are used to reconstruct the emissions as a function of location. The relative amounts of emissions from different locations are reconstructed.

The reconstructed emission distribution is imaged. Any imaging may be used, such as extracting a planar representation from voxels representing the distribution. A multi-planar reconstruction may be generated. In one example, a three-dimensional rendering using projection or surface rendering is performed. The resulting three-dimensional representation is displayed on the two-dimensional screen.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for dead time determination for a gamma camera, the method comprising:

detecting, with the gamma camera, a count rate from a radioisotope source connected adjacent to the gamma camera, the gamma camera configured to detect the count rate at a first energy range;

detecting, with the gamma camera, emissions from within a patient while detecting the count rate, a radioisotope of the radioisotope source being different than any source of the emissions from within the patient, the radioisotope having a greater half-life by a factor of at least ten than a radiotracer generating the emissions from within the patient such that the count rate has a constant known rate, the gamma camera configured to detect the emissions at a second energy range different from and not overlapping with the first energy range;

determining the dead time from the count rate; and correcting a count of the emissions as a function of the dead time, wherein detecting the count rate comprises detecting with the radioisotope source comprising a shielded source having a window in the shielding directed to allow gamma rays to impinge only upon the gamma camera, the shielded source directly connected to a collimator of the gamma camera or the gamma camera.

2. The method of claim 1 wherein detecting the count rate comprises detecting with the radioisotope source being a shielded source connected to emit at a corner of the gamma camera.

3. The method of claim 1 wherein detecting the emissions comprises operating the gamma camera in a fully integrated mode.

4. The method of claim 1 wherein determining the dead time from the count rate comprises calculating a ratio of the count rate to a rate with no system dead time.

5. The method of claim 4 wherein correcting the count comprises dividing the count by the ratio.

6. The method of claim 1 further comprising: generating a single photon emission computed tomograph image as a function of the corrected count.

7. The method of claim 1 further comprising: calculating an activity concentration as a function of the corrected count.

* * * * *